United States Patent [19]

Sun et al.

[11] Patent Number: 4,752,141
[45] Date of Patent: Jun. 21, 1988

[54] FIBEROPTIC SENSING OF TEMPERATURE AND/OR OTHER PHYSICAL PARAMETERS

[75] Inventors: Mei H. Sun, Los Altos; Kenneth A. Wickersheim, Menlo Park; Stanley O. Heinemann, Irvine, all of Calif.

[73] Assignee: Luxtron Corporation, Mountain View, Calif.

[21] Appl. No.: 921,637

[22] Filed: Oct. 22, 1986

Related U.S. Application Data

[63] Continuation-in-part of Ser. No. 791,223, Oct. 25, 1985, abandoned.

[51] Int. Cl.[4] .................. G01K 11/20; G01D 5/34; G01L 9/00
[52] U.S. Cl. .................... 374/161; 374/142; 374/143; 374/131; 73/293; 73/705; 73/714; 250/231 R
[58] Field of Search ............... 374/131, 143, 159, 161, 374/162, 142; 250/227, 231 P, 380, 483.1, 231 R; 356/44, 128, 133; 901/46, 47; 350/96.15; 73/705, 708, 293, 714

[56] References Cited

U.S. PATENT DOCUMENTS

| | | | |
|---|---|---|---|
| Re. 31,832 | 2/1985 | Samulski | 374/131 |
| 3,327,584 | 6/1967 | Kissinger | 356/375 |
| 3,580,082 | 5/1971 | Strack | 73/705 |
| 3,940,608 | 2/1976 | Kissinger et al. | 250/227 |
| 4,118,100 | 10/1978 | Goell et al. | 250/227 |
| 4,128,766 | 12/1978 | Stevens | 250/483.1 |
| 4,223,226 | 9/1980 | Quick et al. | 250/461 R |
| 4,270,050 | 5/1981 | Brogardh | 250/231 R |
| 4,288,159 | 9/1981 | Newman | 374/161 |
| 4,353,259 | 10/1982 | Schneider, Jr. | 73/653 |
| 4,374,328 | 2/1983 | Tekippe et al. | 374/131 |
| 4,376,390 | 3/1983 | Rines | 73/653 |
| 4,379,226 | 4/1983 | Sichling et al. | 250/231 P |
| 4,419,895 | 12/1983 | Fuller | 250/227 |
| 4,427,293 | 1/1984 | Harmer | 356/133 |
| 4,448,547 | 5/1984 | Wickersheim | 374/131 |
| 4,523,092 | 6/1985 | Nelson | 250/227 |
| 4,560,868 | 12/1985 | Brogardh et al. | 250/227 |
| 4,562,348 | 12/1985 | Brogardh et al. | 250/231 R |
| 4,569,570 | 2/1986 | Brogardh et al. | 350/96.1 |
| 4,581,530 | 4/1986 | Brogardh et al. | 250/231 R |
| 4,598,586 | 7/1986 | Danielson | 73/517 B |
| 4,599,711 | 7/1986 | Cuomo | 250/231 P |
| 4,599,901 | 7/1986 | Hirschfeld | 73/705 |
| 4,600,836 | 7/1986 | Berthold, III et al. | 250/231 P |
| 4,652,143 | 3/1987 | Wickersheim et al. | 374/161 |
| 4,678,905 | 7/1987 | Phillips | 250/227 |

OTHER PUBLICATIONS

"Second Generation Fluoroptic TM Thermometer," Wickersheim et al., presented at Digitech '85 of the Instrument Society of America, May 14–16, 1985.
"Advances in Fluoroptic Thermometry: New Applications in Temperature Measurement," Sun et al., presented at Digitech '85 of the Instrument Society of America, May 14–16, 1985.

(List continued on next page.)

*Primary Examiner*—William A. Cuchlinski, Jr.
*Assistant Examiner*—Thomas B. Will
*Attorney, Agent, or Firm*—Majestic, Gallagher, Parsons & Siebert

[57] ABSTRACT

Several specific types of optical sensors capable of measuring temperature, pressure, force, acceleration, radiation and electrical fields, fluid level, vapor pressure, and the like, are disclosed, along with an electro-optical system for detecting the optical signal developed by the sensor. One such probe utilizes a convex shaped structure consisting of an elastomeric material attached to an end of an optical fiber, the elastomeric material being coated with a luminescent material, a combination that is capable of measuring both temperature and pressure. Such a probe is also specifically adapted for measuring surface temperature by making a good physical contact with the surface being measured. Another such probe utilizes a similar structure but of a non-elastomeric material for the purpose of detecting both temperature and either index of refraction of vapor pressure changes. Improvements in other existing sensors of a wide variety of physical parameters other than temperature are also described wherein temperature is simultaneously measured for correcting such physical parameter measurements that are affected by temperature variations.

24 Claims, 4 Drawing Sheets

OTHER PUBLICATIONS

"Improved Surface Temperature Measurement Using Phosphor-Based Fiberoptic Techniques," Wickersheim et al., *Research and Development*, Nov. 1985.

"Tactile Sensors and the Gripping Challenge," Dario et al., *IEEE Spectrum*, Aug. 1985, pp. 46-52.

"Improved Surface Temperature Measurement Techniques for Use in Conjunction with Electronics Processing and Testing," Sun et al., presented at the Semiconductor, Thermal and Temperature Measurement Symposium (Semi-Therm) at Scottsdale, Ariz. on Dec. 10, 1986.

"Fabrication and Investigation of Drawn Fiber Tapers with Spherical Microlenses," Mathyssek et al., J. Opt. Commun. 6 (1985) 4, pp. 142-146.

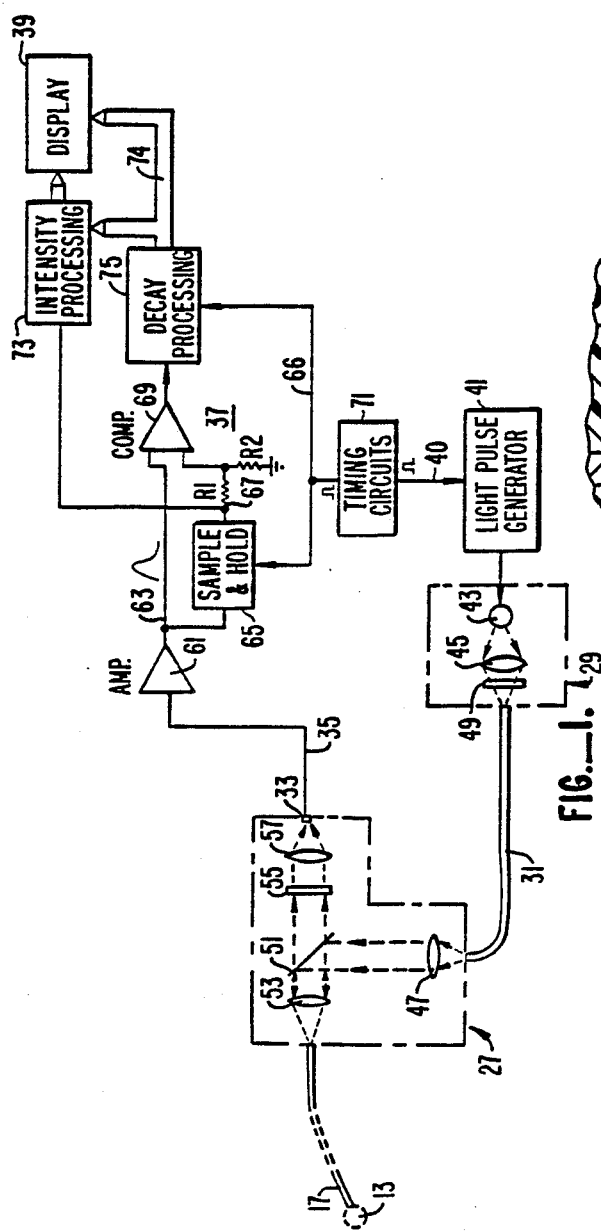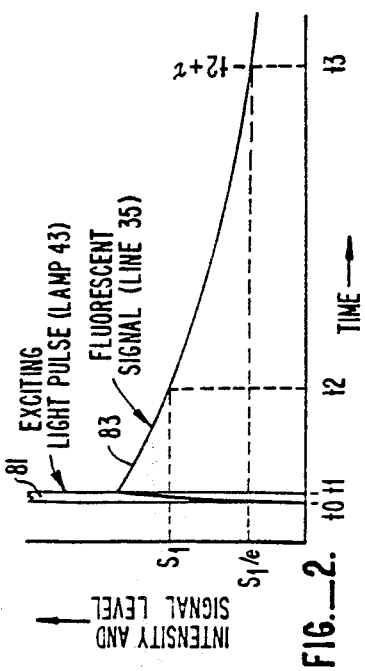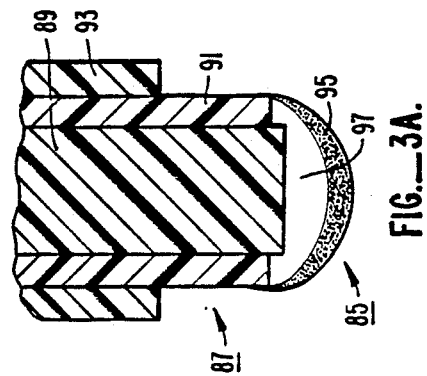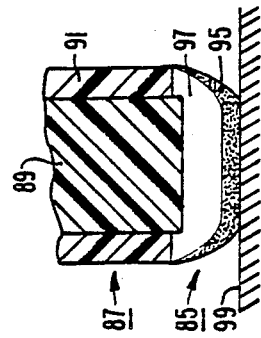

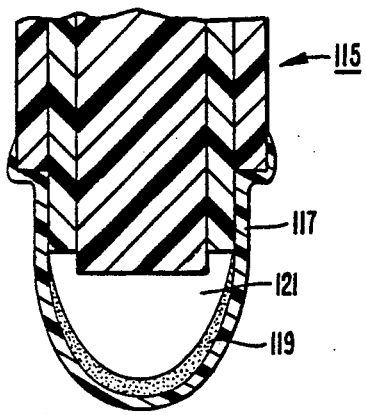
FIG._4.
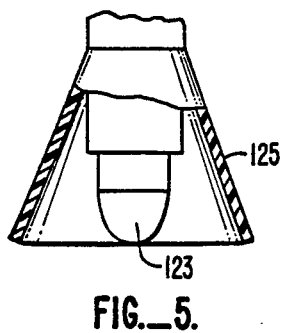
FIG._5.
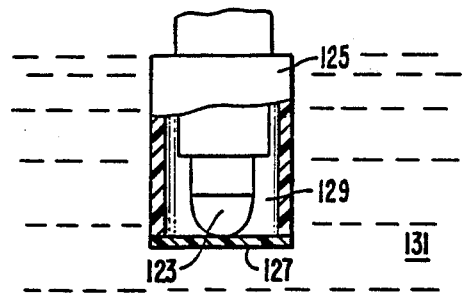
FIG._6.
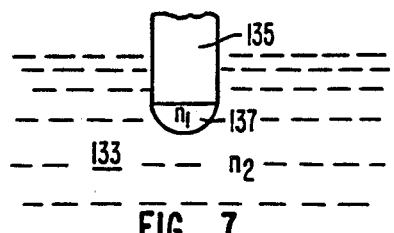
FIG._7.

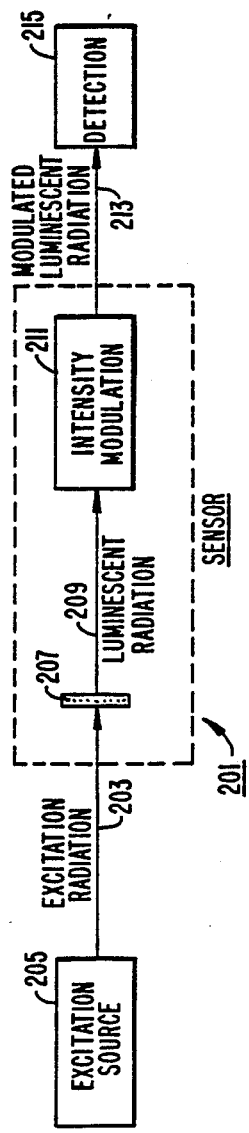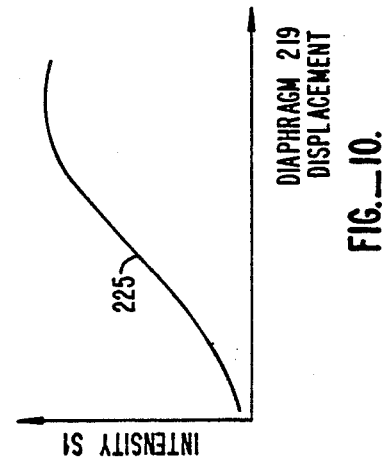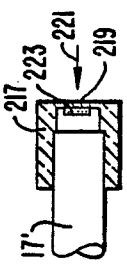

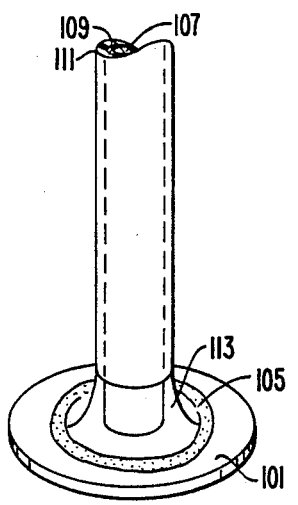
FIG._11A.
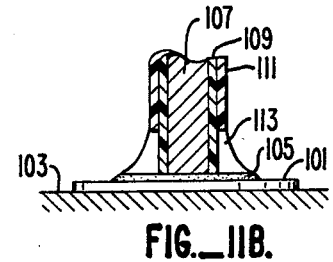
FIG._11B.
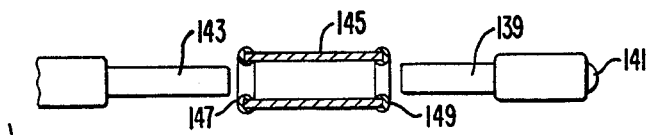
FIG._12.
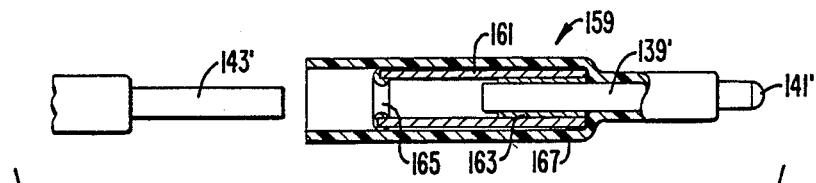
FIG._13.
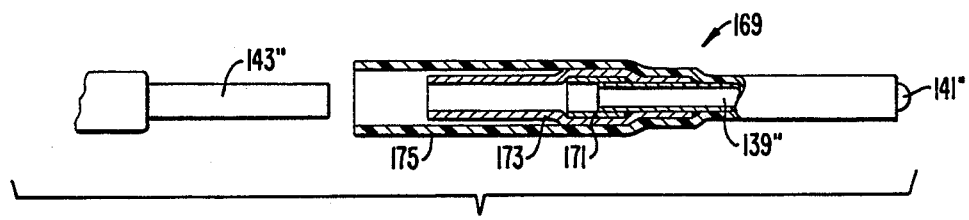
FIG._14.
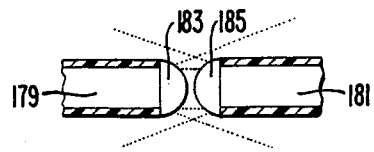
FIG._15.

FIBEROPTIC SENSING OF TEMPERATURE AND/OR OTHER PHYSICAL PARAMETERS

CROSS-REFERENCE TO A RELATED APPLICATION

This is a continuation-in-part of application Ser. No. 791,223, filed Oct. 25, 1985 now abandoned.

BACKGROUND OF THE INVENTION

This invention relates generally to optical sensing of various parameters, and more particularly to optical sensing that includes the use of luminescent material. This invention has two principal aspects, one of which pertains generally to temperature measurement, and the other of which pertains to the general measurement, of a second parameter, such as pressure, force, acceleration, refractive index, or vapor pressure, along with the measurement of temperature.

With regard to the first principal aspect of the present invention, as background, there are a large number of instances where accurate determination of the temperature of a solid is desired or necessary. For example, solid material being processed often requires that its surface temperature be known in order to adjust the parameters of the processing steps. A specific example is in the fabrication of electronic semiconductor devices wherein it is desirable to know the temperature of a surface of semiconductor wafers or other solid materials as they are being processed. Since many semiconductor processing steps are now conducted in a vacuum chamber, rather than in an oven or furnace, the difficulties of measuring surface temperatures are increased. In many cases where it would increase efficiency, quality of the resulting product, or reduce costs, surface temperature should be measured but cannot be by existing techniques because of the difficulty, expense or inaccuracy.

One technique that is used for surface temperature measurements is to attach a small thermistor or a thermocouple to the surface, or to deposit a resistive film on it. This is a very tedious operation and cannot be utilized in routine production applications, or in electrically or chemically hostile environments.

Infrared (I.R.) radiometry is an alternate, non-contact technique for measuring surface temperature by observing the infrared energy emitted from the surface of interest. This technique, however, requires that the emissivity of the surface being measured be known with great accuracy. Otherwise, the temperature measurements are not reliable. Unfortunately, it is difficult to accurately know the emissivity of the surface, particularly in applications where it is changing as a result of processing that surface by etching, coating and the like. In an application to semiconductor wafer processing, it is hard to use I.R. because of the transparency of most semiconductor wafers to those wavelengths, limited accessibility to the chamber in which the processing is taking place, and its poor sensitivity and accuracy at typical wafer processing temperatures.

A more recent technique utilizes luminescent materials that, when properly excited to luminescence, emit radiation with a characteristic that is proportional to the phosphor's temperature. There are two primary categories of luminescent temperature sensing techniques that are currently receiving attention. One such technique involves the detection of the intensity of emitted radiation from a luminescent material in two different wavelength ranges and then ratioing those intensities to obtain a value proportional to temperature. An example of this technique is given in U.S. Pat. No. 4,448,547-Wickersheim (1984). In a second technique, the luminescent material is illuminated with a pulse of excitation radiation and then the decay time, or a quantity related thereto, of the luminescent after-glow radiation is measured. Example of this technique are given in U.S. Pat. Nos. Re. 31,832-Samulski (1985) and 4,223,226-Quick et al. (1980), and in allowed copending application Ser. No. 787,784, filed Oct. 15, 1985, now U.S. Pat. No. 4,652,143 and assigned to the assignee of the present application. The temperature of the luminescent material sensor is determined by either technique, thus providing a determination of the temperature of the environment surrounding the sensor.

These luminescent techniques have been used in two general ways for measuring surface temperature. A first is to attach a layer of the phosphor material in direct contact with the surface whose temperature is to be determined, one form being to paint onto the surface a transparent binder carrying phosphor particles. The phosphor emission is viewed by an optical system positioned some distance from the surface. A shortcoming of this technique is that it is often difficult to implement for many applications since the attachment of the phosphor to the surface may be too permanent and/or there may not be a necessary clear optical path between the phosphor and the optical elements. This technique does have the advantage of detecting temperature in a remote manner and minimizing any surface perturbation, and, for that reason, is advantageous for other applications.

A second category of luminescent sensor surface measurement techniques utilizes a phosphor sensor on the end of an optical fiber. This technique has the advantage of only a temporary contact with the surface being required, but has a disadvantage that, in applications where extremely accurate temperature measurements are required, the optical fiber carries away heat from the surface and also presents an undesired thermal mass that must be heated by the surface being measured. These factors cause the resulting temperature measurements to be offset from the true temperature of the surface and may also slow down the time response of the sensor.

Therefore, it is a primary object of the present invention to provide a surface temperature measurement technique and device that minimizes these difficulties.

With regard to the second principal aspect of the present invention, as background, the measurement of various physical parameters other than temperature, such as force, pressure, acceleration, refractive index and vapor pressure with optical devices is very desirable for many applications where electrically conductive elements must be avoided. For example, one such application of pressure measurement includes an environment of highly volatile liquids or gases where electrical leakage or discharge may be a serious hazard. Medical applications are numerous, especially where miniature catheters are required to measure body fluid pressure in a specific organ or blood vessel. Voltage breakdown during defibrilation may be destructive to many conductive types of pressure transducers and may also create undesirable electrical currents in the patient. There is also the consideration of excessive pressure overload damaging the transducer.

Some of the many techniques used for pressure monitoring range from ceramic piezo-electric discs which generate a voltage when stressed, to similar silicon devices with resistors deposited in many different fashions to form an electrical resistive network which, when deformed, predictably changes the resistance ratio. Shear effect in semiconductors is also being used at this time. Older methods, such as diaphragms with strain gauges or beams attached, are also still widely used. All of these techniques require special insulation and protection methods, both mechanical and electrical, which make the product difficult to manufacture and then still presents some degree of the risks mentioned above.

As a result, optical techniques are also being used to measure various physical parameters other than temperature in order to overcome the operational and structural problems described above. The usual optical technique uses a sensor from which an optical signal of the parameter being measured is communicated along an optical fiber. One example of such an optical fiber sensor is a reflective diaphragm whose position is proportional to the condition being measured, such as force or pressure, and that position modulates the intensity of the light signal passed through the sensor by the optical fiber communication medium. The optical signal proportional to the parameter being measured is then detected at an opposite end of the optical fiber medium. Other fiber optic sensors of force or pressure include those which use beams, the compression of fibers between two plates, vibrating crystals which modulate reflected light, and coherent-light phase shift and amplitude modulation effects. Similar types of sensors have been employed to measure other physical parameters than force or pressure, such as displacement or alignment of an element, mass or weight, magnostrictive or electrostrictive effects, and the presence of contamination.

The manufacture of all these types of sensors generally require delicate mechanical structures that are time consuming to assemble and test. Therefore, it is another object of the present invention to provide a simple, sturdy and economical technique for measuring such parameters.

It is a further object of the present invention to provide an optical measurement technique and device capable of simultaneous measurement of temperature and a second physical parameter.

SUMMARY OF THE INVENTION

These and additional objects are provided by the various aspects of the present invention which are briefly described here. According to a first principal aspect of the invention, a temperature sensor adapted for physically contacting a surface is formed by a layer of transparent elastomeric material attached to the end of the fiber, and a thin layer of phosphor material is attached to a surface of the elastomer removed from the fiberoptic end. When such a probe is brought into contact with the surface whose temperature is to be measured, the phosphor layer conforms to that surface directly and is thermally insulated from the fiberoptic end by the elastomer layer. This significantly reduces the amount of heat transferred from the surface through the optical fiber during the temperature measurement, and thus greatly increases the accuracy of the temperature measurement. The use of elastomeric material also assures close contact between the phosphor layer and the surface, thereby to further increase the accuracy of the measurement by eliminating any insulting voids between the phosphor and the surface. The thermally isolated phosphor has a very low thermal mass and thus is heated to the temperature of the surface in a very short time.

These surface temperature measuring techniques are described generally by two articles that describe the work of the assignee of this application that is described herein: Wickersheim and Sun, "Improved Surface Temperature Measurement Using Phosphor-Based Fiberoptic Techniques"; and Sun, Wickersheim and Kim, "Improved Surface Temperature Measurement Techniques for Use in Conjunction with Electronics Processing and Testing." These articles are expressly incorporated herein by reference.

According to a second principal aspect of the present invention, existing optical sensors of physical parameters or conditions other than temperature, such as force, pressure, displacement, acceleration, refractive index, vapor pressure and the like, are provided with a quantity of temperature sensitive luminescent material in the path of the optical signal.

As an example of such an improved sensor structure, an existing type of mechanical sensor, wherein a light beam is reflected from a deformable structure that moves an amount toward or away from an end of an optical fiber an amount dependent upon the magnitude of the parameter being measured, has a layer of luminescent material attached to the deformable structure at a location where the light beam strikes it. The illuminating light is chosen to excite the layer to luminescence, and the resulting luminescent radiation is passed back through the optical fiber to a detecting station. Since the excitation and luminescent radiation are at different wavelengths, they can both be communicated along a single optical fiber, thus allowing the fiber/sensor structure to be very small. The luminescent radiation that is detected at an opposite end of the optical fiber contains separable information of the value of the physical parameter and of the temperature of the sensor. These two items of information may be used independently, or, alternatively, the temperature information may be obtained for the purpose of correcting the reading of the physical parameter for any temperature dependent effects.

As another example of such an improved sensor structure, an existing type of sensor includes a nondeformable optical surface adapted to be immersed in a material whose index of refraction is desired to be determined. The amount of light interaction with the surface is related to the index of refraction of a material in which the sensor is immersed. An application of the present invention is to provide luminescent material at that surface in order to develop an optical signal from which the sensor's temperature can be determined, in addition to determining index of refraction.

The two principal aspects of the invention are cooperatively combined in the form of a specific sensor for measuring temperature of an object contacting it, as well as the pressure being exerted at the contact of the sensor and object. As the surface temperature measuring probe according to the first pricipal aspect of the present invention is pushed against a surface, its domed elastomeric tip is deformed, thus altering the optical coupling between the fiber and the phosphor layer. The result is that the total luminescent radiation that is detected is related to the amount of the tip deformation, and thus to the pressure against it. The ability to simultaneously measure temperature and pressure with such a single sensor is very advantageous. One application where such a device is highly useful is in robotics. Such a sensor has many of the characteristics of a human finger since the primary parameters sensed by a finger end are temperature and pressure. Other applications include fluid pressure measurement and a related fluid level measurement, both accomplished by submersing the sensor in the liquid.

Additional objects, advantages and features of the various aspects of the present invention are set forth as part of the following description of the preferred embodiments thereof, which description should be taken in conjunction with the accompanying drawings.

BRIEF DESCRIPTION OF THE DRAWINGS

FIG. 1 is an electro-optical schematic diagram which illustrates an instrument capable of carrying out the various aspects of the present invention;

FIG. 2 is a characteristic curve showing decay time versus temperature in the operation of the system of FIG. 1;

FIGS. 3A and 3B show an optical fiber sensor for measuring surface temperatures according to a first principal aspect of the present invention;

FIG. 4 shows a modified version of the sensor of FIGS. 3A and 3B that measures pressure as well as temperature;

Each of FIGS. 5 and 6 show yet different designs of an optical fiber sensor that are capable of measuring pressure as well as temperature;

FIG. 7 shows the use of an optical fiber sensor for measuring refractive index of a surrounding fluid;

FIG. 8 schematically illustrates a second principal aspect of the present invention wherein luminescent material is added to a physical parameter sensor in order to obtain values of both the physical parameter and temperature of the sensor;

FIG. 9 is a specific example of a sensor according to FIG. 8;

FIG. 10 is a curve that shows a portion of the operation of the sensor of FIG. 9;

FIGS. 11A and 11B show a surface temperature measuring sensor of a different design;

Each of FIGS. 12, 13 and 14 illustrate different specific designs for a disposable sensor that is removably attachable to a fiberoptic end; and FIG. 15 illustrates a possible modification of the disposable probe embodiments of FIGS. 12-14.

DESCRIPTION OF THE PREFERRED EMBODIMENTS

Referring initially to FIG. 1, an electrooptical detection and processing system is generally explained. This system can utilize the various probes, and implement the various measuring techniques, of the present invention. A generalized sensor 13 is carried by one end of an optical fiber 17. The sensor 13 contains luminescent material that is excited to luminesce by directing visible or near visible light along the optical fiber. The resultant luminescent radiation, in a visible or near visible radiation band, is usually, but not necessarily, of longer wavelength than the excitation radiation. The luminescence is directed from the sensor 13 along the optical fiber communication medium 17 to the measuring instrument. The fiber medium 17 can include a single fiber or a number of fibers.

An optical system 27 connects the fiber medium 17 with a source 29 of excitation radiation through another fiber medium 31. The optical assembly 27 also communicates the luminescent radiation from the fiber medium 17 to a detector 33 that is electrically connected by a conductor 35 to an electronic processing system 37. The processing circuits 37 convert, by reference to an empirically established conversion table, the luminescent radiation decay characteristics of the sensor 13 into a temperature that is indicated at a display 39. The timing of an excitation pulse driving circuit 41 is controlled by timing circuits of the processing circuits 37 through a line 40. The circuit 41 is connected to a flash lamp 43 of the excitation source 29. The periodic pulse from the lamp 43 is imaged by a lens 45 through a filter 49 into an end of the optical fiber transmission medium 31. The filter 49 limits the wavelengths to the range that is useful to excite the particular luminescent sensor 13.

The optical system 27 includes a lens 47 for collimating the excitation light at an end of the fiber medium 31. The collimated excitation pulses are directed to a beam splitter 51 and thence through a lens 53 into an end of the optical fiber transmission medium 17 for exciting the sensor 13 to luminescence.

The luminescent radiation from the sensor 13 is returned by the fiber medium 17 to the instrument where the returning radiation is again collimated by the lens 53. The collimated beam passes through the beam splitter 51 and an optical filter 55 which limits the radiation passing through it to the wavelength band of luminescence of the sensor 13. The wavelength bands allowed to pass by the filters 49 and 55 will ideally be non-overlapping. A lens 57 focuses the filtered luminescent radiation onto the detector 33 which may be a photodiode that is sensitive to the range of wavelengths passing through the filter 55.

It is the decay time of the luminescence, after the excitation pulse, that is measured by this instrument example. Many particular electronic methods for measuring the decay time of such an exponential curve are well known and can be applied in this instrument. FIG. 2 shows one instrument cycle, an excitation light pulse 81 followed by a decaying luminescent signal 83. One such technique is to measure between two specific times the area under the durve 83. Another is to measure the voltage value of the curve 83 at a particular time after the excitation pulse is completed and then measure how long it takes for that voltage to fall to a level equal to the reciprocal of the natural logarithmic base times that voltage. These techniques are easily accomplished by standard analog and microprocessor calculating systems which may be incorporated as part of the processing circuits 37.

The specific example of processing circuits 37 shown in FIG. 1 will now be generally described for implementing the specific technique shown in FIG. 2. The excitation pulse 81, generated by the lamp 43 (FIG. 1), occurs between the times t0 and t1. The signal in line 35 at the output of the detector 33 is illustrated as curve 83 in FIG. 2. The circuits of FIG. 1 are adapted to measure the declining voltage at a time t2 that occurs a preset interval after the beginning of the excitation pulse 81 at time t0. That voltage is identified on FIG. 2 as $S_1$. A second voltage $S_1/e$ is then calculated. When the signal represented by the curve 83 falls to that level, the time t3 at which that happens is noted. The interval between t2 and t3 is the decay time period of the curve 83, the desired quantity that can then be converted to temperature.

In order to accomplish this, the detector output in line 35 is connected to an input of an amplifier 61 whose output in a line 63 is connected as one of two inputs of a comparator 69. The amplified signal in the line 63 is also applied to an input of a sample and hold circuit 65, which stores a single value of the input signal at the time it receives a sampling pulse in a line 66 from timing circuit 71. The input voltage held by the circuits 65 is presented at an output 67 that is applied to a voltage divider, namely series connected resistors R1 and R2. The second input to the comparator 69 is connected to a junction between series resistors R1 and R2. The values of R1 and R2 are selected so that the voltage at this juncture is equal to the voltage in line 67 divided by the natural number "e".

Decay processing circuits 75 are provided for measuring the time between t2 and t3 from its two inputs shown. That time difference is directly related to temperature of the luminescent material in the sensor 13 and is converted by an empirically determined table that is part of the circuits 75. Intensity of processing circuits 73 receive a signal from the output 67 of the sample and hold circuit 65 and convert this total luminescence signal into another parameter described hereinafter, such as pressure or refractive index. A display device 39 shows these results.

A preferred luminescent material for the particular sensors to be described, for use as a sensor 13 in the system of FIG. 1, is a phosphor made of a host of either magnesium germanate or magnesium fluorgermanate, activated with tetravalent manganese. The concentration of the activator (based on starting materials) should be within the range of from 0.05 to 5.0 mole percent, approximately one mole percent being preferable. The concentration of the activator controls the decay time and the intensity of luminescence. Magnesium fluorogermanate is sold commercially for use in lamps as a red color corrector in high pressure mercury lamps. Composition of a manganese activated magnesium germanate phosphor for use in the sensor 13 is $Mg_{28}Ge_{10}O_{48}$(1 mole % $Mn^{+4}$). Composition of a manganese activated magnesium fluorogermanate phosphor for such use is $Mg_{28}Ge_{7.5}O_{38}F_{10}$(1 mole % $Mn^{+4}$).

Each sensor to be described preferably forms a luminescent layer from a powder of such a phosphor. That is, rather than one or a few crystals, a large number of individual grains or crystallites of the size of a few microns, typically from one to ten microns, held together by an inert, transparent binder to form any of the particular forms of sensors to be described. Each grain has a temperature dependent luminescence that contributes to the total observed luminescence although the variation from cystallite to cystallite is small.

One specific technique and probe design according to the present invention is illustrated in FIGS. 3A and 3B. A sensor 85 is attached at an end of an optical fiber 87. The sensor 85 is shown to be attached to a single fiber, but can alternatively be attached to ends of multiple fibers held together in a bundle, if desired for additional light transmission or some other reason. The single fiber is usually preferred, however, because of its very small size. The typical optical fiber includes a cylindrical core 89 that is surrounded by a thin cladding 91. The diameter of the combination is typically 0.5 millimeter. The core 89 is preferably made of fused quartz or glass for high temperature applications. An alternative plastic material that is used for the core 89 for lower temperature measurements is even less heat conductive. The core 89 and cladding 91 are surrounded by an opaque protective jacket 93. What has been described is commercially available optical fiber.

Powdered phosphor material of the type described above for use as a temperature sensor is held by a binder material in a layer 95 at the end of the optical fiber 87. But rather than attaching that layer directly to the end of the core 89, as is usually done, an optically clear material layer 97 is interposed therebetween. If the material of the layer 97 has less heat conductive characteristics than that of the fiber core 89, then the accuracy of the temperature readings is increased because less heat is carried away by the fiber from the phosphor and the surface whose temperature is being measured.

The material 97 must be optically clear; that is, it must not significantly attenuate either the excitation radiation being directed from the fiber against the phosphor sensor 95, or the resulting luminescent radiation directed into the fiber from the phosphor. The binder used in the layer 95 must also be optically clear. It is usually desirable to select the material for the layer 97 to have a refractive index that is very close to that of the fiber core 89. Further, if the layer 97 is formed into a lens shape, as shown in FIG. 3A, optical coupling is improved between the phosphor and the fiber, for both excitation and luminescent radiation, thus increasing the amount of luminescent radiation that is detected at the opposite end of the fiber for a given amount of phosphor. Alternatively, the convex shape allows the amount of phosphor in the layer 95 to be reduced.

A result of use of the thermal insulating layer 97 is to present to the surface, or other environment whose temperature is being measured, a very low thermal mass of the phosphor which is well insulated from the heat conducting fiber. Hence, the response time of the temperature sensing probde of FIG. 3A is extremely short. That is, it takes very little time for the phosphor particles to reach temperature equilibrium with that of the surface it is contacting or other environment in which it is placed. By utilizing light gathering qualities of the insulating medium 97, as a result of forming it into a hemispherical or other convex shape, the phosphor thickness can be reduced for a given luminescent signal level, thus minimizing the thermal gradient through the phosphor layer.

The probe of FIG. 3A can be made especially useful for surface temperature measurements if it is made from an elastic material. As shown in FIG. 3B, the use of an elastic material for the layer 97 allows the phosphor layer 95 to be forced into very close contact with a surface 99 whose temperature is being measured. This close contact is produced by light pressure. This eliminates any voids or pockets of air that might ordinarily be trapped between the phosphor layer 95 and the surface 99, thus further improving the accuracy of the temperature reading. Such a probe with a compressible layer 97 is especially advantageous for all surface temperature measurements, particularly when the surface 99 is a silicon wafer, being processed in a hostile environment, and especially when that environment is a vacuum.

In addition to the desirable characteristics for the layer 97 described above, the elastomeric material should have a memory. That is, the material should return to its original, uncompressed state shown in FIG. 3A when the force against it is removed. This desirably occurs when the fiber 89 is pulled away from the surface 99, so that the sensor is immediately ready for a new measurement. The elasticity and compression strength chosen for the layer 97 material is that which will bring about the close surface contact between the phosphor layer 95 and the surface 99 under the pressure conditions anticipated for its use. The material should not, however, be so soft that the phosphor layer becomes too close to the fiber end when pressed against the surface, or that the tip is easily damaged.

For a temperature sensor designed to be held by hand, or a probe holder, against a surface, a silicone elastomer manufactured and sold by Dow Corning under their number 96-083 is quite satisfactory. The probe is formed by first stripping back the jacket 93 and polishing the core 89, as shown in FIG. 3A. The elastomeric material in a liquid state is then spread on a glass plate in a layer that approximates the maximum thickness of the layer 97. In a specific example, this thickness is about 0.004 inch. The material is viscous enough to remain in such a layer on the glass plate, for at least long enough to enable the manufacturing process to be completed. The free end of the fiber 87 is then brought into contact with the elastomeric material layer. Since it has good properties of adhesion to the glass fiber core and cladding, a portion of the layer attaches itself to the fiber end. When the fiber end is removed from the layer, the convexly shaped solid 97 as shown in FIG. 3A results from the surface tension of the material.

The next step is to cure the elastomer by placing it in a heated oven. The next step is to mix the desired phosphor particles in another batch of the same elastomeric material. This provides good adhesion between the phosphor layer and the layer 97 and also to assure that the refractive index of the elastomer binder in the layer 95 is the same as that in the layer 97. This mixture is again spread on a glass plate to a thickness approximating the desired thickness of the sensor layer 95. In the specific example being described, this thickness is preferably in the range of 0.002-0.003 inch. The elastomeric binder of the layer 95 is then cured by placing in a heated oven. As an alternative construction, the luminescent material sensor 95 can be in a form of a solid, flexible film without any binder. The useful temperature range measurable by the sensor described with respect to FIGS. 3A and 3B, with the powdered phosphor previously described, is $+50°$ C. to $+200°$ C.

As an alternative to this manufacturing technique, the sensor element 85 could be first formed separately and then attached to the end of the optical fiber 87. However, because of the very small dimensions involved, the method described above is preferable.

The temperature sensing probe of FIG. 3A is preferably used with the instrument previously discussed with respect to FIGS. 1 and 2. The selected one of those probes becomes the sensor 13 of FIG. 1, and the fiber to which it is attached becomes fiber 17 of FIG. 1. The temperature detection technique, when a probe of FIG. 3A is used with the system of FIG. 1, is to detect the luminescent decay time, as described in detail above. Alternatively, an intensity ratioing technique as described in U.S. Pat. No. 4,448,547-Wickersheim (1984) may be employed. Indeed, the structure of the probe of FIG. 3A is independent of the precise luminescent material used or technique for extracting temperature information from the luminescent radiation. The advantage of these probes are realized for a wide variety of materials and detection techniques.

The use of the elastomeric element 97 in the probe embodiment of FIGS. 3A and 3B also allows the amount of compression of the element 97 to be measured by measuring the total luminescent light intensity from the phosphor sensor 95 in the instrument at the other end of the optical fiber 87. The total amount of luminescent radiation that is coupled between the layer 95 and the end of the optical fiber core 89 is a function of the geometry of the coupling material 97. When it is flattened, as shown in FIG. 3B, that optical coupling is changed. A decrease in total measure fluorescent light intensity is related to an increase in the force, or pressure, being exerted against the probe tip.

The ability to simultaneously measure both temperature and pressure by a single optical sensor has many exciting applications, such as in robotics or level sensing. The total amount of light can be measured by the instrument described with respect to FIG. 1. Since the time t2, at which the sample and hold circuit 65 obtains an amplitude value of the luminescent signal, occurs at the same time with respect to the excitation light pulse 81 for each cycle, that value is proportional to the total amount of intensity. An apropriate processing circuit 73 empirically relates that total intensity to force or pressure at the probe tip end, as desired. This does not interfere with the temperature determining decay time processing, thereby resulting in the ability to provide the display 39 with both temperature and pressure information from the single sensor.

Since the total luminescent intensity is also affected by a number of other variables, such as the intensity of the excitation light source 43, fiber attenuation differences, and phosphor layer thickness, steps to limit these variables are taken. Calibration of the instrument and probe against a reference reduces the effects of these factors. Another such step, in the case of a flash excitation source, is to present a pressure reading as a result of averaging the total luminescent intensity for a number, such as ten, of luminescent decay cycles. Also, ambient light conditions in the area where such a probe is being used can affect the results if enough light enters the optical fiber end at the sensor 85. A limited angle of acceptance that is characteristic of optical fibers, however, minimizes these effects in many cases, but in other cases it is desirable to provide some means of shielding the end of the optical fiber from ambient light.

A probe shown in FIG. 4 is a modified version of that of FIG. 3A and includes such a light shield. A fiber 115, having the same structure as a fiber 87 of FIG. 3A, includes a light blocking, opaque coating 117 over the entire sensor in order to prevent any ambient light from entering the end of the fiber. Only light from an internal phosphor sensor 119 is received by the optical fiber end, through an elastomeric tip 121. The phosphor sensor layer 119 is made substantially the same as that of the layer 95 of FIG. 3A. The elastomeric element 121 of the FIG. 4 embodiment is, however, made to be more elongated than the counterpart element 97 of the FIG. 3A embodiment. The elongated elastic element provides for a greater amount of deformation, and thus for a wider range of pressures that can be measured. The degree of elongation and material characteristics are chosen to obtain the desired sensitivity. The sensor shown in FIG. 4 is made the same way as described for the sensor FIG. 3A, except, of course, the liquid elastomer layer used for forming the tip 121 needs to be appropriately thicker. Also, a final step of forming the light opaque shield 117 is performed, preferably by dipping in a thicker. Also, a final step of forming the light opaque shield 117 is performed, preferably by dipping in a pigmented elastomer in liquid form and then allowing it to cure. The characteristics of an elastic memory and low hysterisis are important for the layer 121 when measuring pressure.

Although the sensor embodiment of FIG. 4 blocks the ambient light, it does so at the expense of temperature accuracy by positioning the layer 117 between the phosphor sensor layer 119 and a surface against which it is pressed for measuring both temperature and pressure. Another embodiment is shown in FIG. 5 wherein a sensor 123 is constructed exactly like that shown in FIG. 4, except the light shield layer 117 is eliminated. Instead, an opaque light shielding skirt 125 is attached to the fiber near its end. The skirt 125 is made from a flexible plastic so that it does not interfere with applying pressure of the sensor 123 against a surface whose temperature is being measured.

FIG. 6 illustrates yet another embodiment of a pressure and temperature sensor that is especially adapted for use in liquids. The sensor 123 is, in this case, surrounded by a rigid cylinder 125 that is sealed to the fiber end at its upper end. A flexible diaphragm 127 covers the open bottom end of the cylinder 125. A void 129 is sealed within the cylinder 125. A controlled amount of air pressure is introduced into the void 129. Therefore, when the sensor of FIG. 6 is submersed in a liquid bath 131, the flexible diaphragm 127 is deflected an amount dependent upon the pressure differential from the liquid 131 and the region 129 within the temperature sensor. This deflection then causes compression of the elastomeric element that is part of the sensor 123, thus affecting the total luminescent light that is detected as proportional to pressure. This sensor can be used for measuring liquid pressure as an end in itself, and also may be used to measure the level of the liquid in which it is submersed since that is proportional to the pressure being detected. In any such application, temperature of the liquid at the location of the sensor 123 can also be measured, if desired.

A sensor and technique for measuring the refractive index of a fluid 133 is shown in FIG. 7. The usual optical fiber 135 is terminated at a sensor 137. The sensor 137 is of a design similar to the sensor 85 of the probe of FIG. 3A, except that for this application it is preferable that the element 97 be hard and non-compressible. That element has a refractive index $n_1$. It has been found that the total amount of luminescent radiation entering the optical fiber 1 depends upon the difference between the refractive index $n_1$ of the sensor 137 and a refractive index $n_2$ of the fluid 133. The intensity processing circuit 73 of FIG. 1 can then be utilized to read from the total luminescent intensity the refractive index $n_2$. Temperature can additionally be simultaneously measured, in the manner discussed above. It is desirable that such an index of refraction measurement be independent of liquid pressure. Therefore, the use of a hard, non-deformable tip element 137 is desired for this application.

There are applications where it is desired to measure the refractive index of a fluid as an end in itself. Additionally, vapor pressure of the fluid 133 can be measured since its refractive index is proportional to vapor pressure. Measurement of humidity can also be made by placing the sensor 137 in a water vapor environment. Further, the level of a body of liquid can be determined by measuring the gradient of the vapor above the surface.

Turning now to the second principal aspect of the present invention, a temperature measurement ability is added to existing types of optical sensors of other physical parameters. One class of such sensors measures parameters that can be determined by physical deformation of the sensor. Such parameters include force, pressure, acceleration, displacement, and the like. Another class of such sensors measures parameters from detectable optical changes of a medium only. Such parameters include index of refraction, vapor pressure, intensity of ionizing radiation, intensity of a magnetic field (and thus an electrical current), and the like.

There have been many recent developments of such optical sensors and transducers. Most of these provide indications of the condition or parameter being measured that vary to some degree as a function of the temperature of the sensor. Measuring elements within the sensor, for example, expand and contract with changing temperature, and this can affect the optical signal output. Complicated techniques and structures are employed to either eliminate the effect of temperature on such measurements or to compensate for it in some way such as by frequent calibration. Also, the sensitivity to the parameter may vary with temperature.

According to the present invention, temperature dependend luminescent material is added to such an existing type of physical parameter sensor so that its output signal also indicates the sensor's temperature, in addition to indicating the physical parameter being measured. The temperature information can be used to correct the signal of the physical parameter. Also, in applications of the sensor where temperature is also desired to be observed independently, it is being measured simultaneously with the measurement of the physical parameter.

Referring to FIG. 8, a generalized view of a system using such a sensor is given. A sensor 201 is illuminated by electromagnetic radiation in or near the visible beam, as indicated at 203. That radiation is generated by a source 205, such as a flash lamp. Within the sensor is a quantity of temperature dependent luminescent material 207 upon which the radiation 203 is incident. The material 207 emits luminescent radiation indicated at 209 that is of a different wavelength than that which causes it to be excited to luminescence. It is the luminescent radiation 209 that is modulated by an element of the sensor indicated at 211 that responds to the physical parameter or quantity being measured. As an example, an intensity modulator 211 can be a diaphragm that moves in response to changing pressure being measured. The intensity of the light reflected from the diaphragm is proportional to the amount of pressure against it. Such an output signal is indicated at 213 from which a detector 215 extracts information of pressure or other physical parameter being measured, as well as temperature.

The way in which that can be done is best illustrated by reference to a specific example shown in FIG. 9. A single optical fiber 17' carries a cylindrical sleeve 217 attached at one end thereof. An enclosed end wall 219 of the sleeve 217 is made to be thin enough that it responds by bending to force or pressure indicated by an arrow 221. Coated on the inside of the thin end surface is a layer of temperature sensitive luminescent material 223. The force or pressure being measure causes the luminescent material 223 to move toward and away from an end of the optical fiber 17'. The curvature of the end surface is also changed by changing pressure or force. The end piece 217 can be fabricated from stainless steel, quartz or single crystalline silicon, as examples.

Changing position and curvature of the end piece 219 with respect to the end of the optical fiber 17', although very slight, does create detectable differences in intensity of the luminescent radiation that is captured within the angle of acceptance of the optical fiber 17' end. Both this total intensity, which is proportional to the force of pressure being measured, and a decay time value of the luminscence, which is proportional to the temperature of the sensor, are preferably obtained by the system illustrated with respect to FIGS. 1 and 2, and previously described in detail. The optical fiber 17' of FIG. 9 becomes the fiber 17 of the system of FIG. 1. The temperature of the luminescent material 223 can be determined with precision by monitoring the intensity decay characteristics after an excitation pulse has terminated. An intensity signal S1 at point 67 of FIG. 1 is the varying intensity quantity that is measured as being proportional to the force or pressure 221. A curve 225 of FIG. 10 illustrates the variation of that signal with displacement of the diaphragm 219.

In most sensors, the signal of curve 225 is also temperature dependent, but the technique of the present invention allows the effect of temperature to be automatically removed from the signal proportional to displacement. Referring to FIG. 1, a temperature output signal in line 74 is also applied to intensity processing circuit 73 where that compensation takes place. One technique for effecting that compensation is to have a plurality of look-up tables within the processing circuit 73 for converting the signal S1 at point 67 into a displayable quantity, a different look-up table for each temperature within a given range of temperatures that might be indicated in line 74. Of course, in addition to using the temperature information to compensate for temperature errors in the physical parameter readings, it may be desired to directly display the temperature, as shown in FIG. 1.

The example sensor in the form of a probe shown in FIG. 9 can use multiple fibers if additional intensity is required. But an advantage of the present invention is that a single fiber 17' is generally quite adequate. The excitation and luminescent radiation can be optically separated, even though both travel in a single fiber, since they are in separable wavelength ranges. The use of a single fiber allows very small sensors and probes to be constructed, a primary goal in many applications such as in medical instrumentation wherein the probe must be inserted into a patient through a needle or vein.

The example of displacment detection as used in sensors for force and pressure can be found in many different specific forms in the literature and on the market. Examples include the following U.S. Pat. Nos: 3,327,584-Kissinger (1967); 3,940,608-Kissinger et al. (1976); 3,580,082-Strack (1971); and 4,600,836-Berthold III et al. (1986). In these specific prior art mechanical sensors, and in similar types, great benefit is obtained by the addition of a layer of temperature dependent luminescent material to the reflective surface of their respecitve diaphragms, according to the present invention. It should also be noted that the elastomeric sensor described with respect to FIGS. 3-6, when utilized to measure both temperature and pressure, is another example of the generalized system of FIG. 8.

The diaphragm deflection, light reflecting type of transducer discussed with respect to FIGS. 8 and 9, however, is only one of many specific types of optical transducers that can benefit from the present invention. Accelerometers utilizing a moving reflective surface or a shutter type of arrangement to modulate the light intensity are described in the following U.S. Pat. Nos: 4,376,390-Rines (1983); 4,149,895-Fuller (1983) and 4,353,259-Schneider, Jr. (1982). In the case of existing optical transducers that do not employ a reflective surface but rather modulate the intensity of radiation by a transmission technique, such as the changing effective alignment of optical fiber ends, the luminescent layer can be positioned where the excitation radiation strikes one side, and the luminescent radiation is observed and utilized from the other side. An example structure is the coating of the luminescent material onto the end of an optical fiber is the three accelerometer patents identified immediately above.

Another type of transducer that is commonly utilized relies upon a vibrating element from which light is reflected. The amplitude and frequency of vibration are affected by the magnitude of the physical parameter or other quantity being measured. An example of this is a transducer described in copending United States patent application Ser. No. 612,060, filed May 18, 1984, now U.S. Pat. No. 4,678,905 and assigned to the assignee of the present application, that is adapted to measure pressure, temperature, acceleration or force. This type of sensor similarly benefits from application of a temperature dependent luminescent layer to the reflecting surface of the vibrating element, according to the present invention.

The examples given above are of mechanical sensors. The technique can also be applied to purely optical sensors in the same way. This second class of sensors includes, as an example, that described with respect to FIG. 7, wherein the refractive index of the surrounding material is determined without any moving element, through a detectable optical change. The temperature of the sensor can also be independently and simultaneously determined, as previously described. Many existing optical sensors can have luminescent material added in order to add temperature information to the optical signal from which the magnitude of another parameter can be measured. An example is a device that measures the intensity of a magnetic field by Faraday rotation of the plane of polarization by a sensing element, the electrical current producing such a magnetic field sometimes being the end quantity that is desired to be measured. Another example of an existing optical sensor to which a luminescent layer can be added is one that measures the intensity of ionizing radiation using a scintillation material and scintillation counting techniques. Yet another example of such an optical sensor measures the intensity of electric fields by means of the Pockels effect.

Therefore, it can be seen that the applications of the present invention to existing sensors and transducers by the addition of luminescent material to provide a temperature sensing capability, are numerous. No attempt is made here to list all such beneficial applications of the present invention, for it is too long.

Referring to FIGS. 11A and 11B, an alternative temperature probe is described for use in surface temperature measurement applications. In this case, a very thin, flat, rigid disc 101 is adapted for contacting a surface 103 whose temperature is to be measured. A layer 105 of phosphor material in an opticallay clear binder, such as a low melting point glass, liquid silicate, or the elastomeric material described above, is attached to one side of the disc 101. An end of an optical fiber including a core 107, cladding 109, and a jacket 111, is held in optical communication with the phosphor layer 105 by a flexible attachment layer 113 that is preferably optically clear. It is desired to allow the fiber to tilt with respect to the disc 101 without breaking the mechanical or optical connection. The disc 101 is preferably made of sapphire, but can be made of other hard, thermally conductive materials as well.

The advantage of the structure shown in FIGS. 11A and 11B is that the phosphor layer 105 will be held close to and parallel with the surface 103 whose temperature is to be measured, even if the optical fiber cannot be held exactly perpendicular with the surface 103. The probe of FIGS. 3A and 3B works best if that perpendicular relationship with the surface is maintained. With the embodiment of FIGS. 11A and 11B, the fiber may be tilted with respect to the disc 101, but since the area of the phosphor sensor 115 is quite large, there will always be a full quantity of phosphor within the field of view of the fiberoptic end no matter what angle results within a range of reasonable angles.

The optical sensors described are often used in hostile environments which require periodic replacement of the sensor. If the sensor is attached to an end of a long optical fiber, the expense and inconvenience of discarding the sensor is increased. It is preferable, therefore, in many applications, to provide the sensors described above, and others, in the form of relatively short probe that is easily attached to and removed from an end of an optical fiber that is connected to the measuring instrument, without the necessity of using complicated or expensive connectors.

One such very elementary arrangement is shown in FIG. 12. A short length of optical fiber 139, in the neighborhood of less than a few inches long, is provided with its protective jacket partially stripped. The remaining core and cladding portions of the fiber have a sensor 141 attached to one end. The sensor end 141 can be any of those discussed above, if desired for the particular advantages and applications for which they are best suited, or can be any other type of known luminescent sensor of temperature or any other paramater. In order to optically couple the opposite end of the short fiber length 139 with an end 143 of a longer fiber that is optically connected with the measuring instrument, a rigid cylindrical element 145 is employed that has highly concentric flexible O-rings 147 and 149 at each of its ends. The internal diameter of the cylindrical member 145 is made to be very precise and only slightly larger than that of the optical fibers 139 and 143, which can then be inserted through one of the O-ring seals into the cylinder 145. This arrangement holds the ends of the fibers 139 and 143 together to provide optical communication between them. When the sensor 141 needs to be replaced, the small optical fiber piece is removed and a new one inserted.

Referring to FIG. 13, another form of a detachable probe is illustrated. The elements that are common with the embodiment of FIG. 12 are given the same reference number with a prime (') added. In this case, the short fiber length 139' is permanently affixed within a rigid cylindrical sleeve 161 by an appropriate adhesive material 163. An O-ring 165 is attached at another end of the cylinder 161 for receiving the optical fiber 143' without its jacket. A jacket 167 which has a much larger diameter at its open end than that of the rigid cylinder, is formed on the probe assembly 159 to guide the fiber 143' during coupling, and also for light tightness and strength. The hollow cylindrical members 145 (FIG. 12) and 161 (FIG. 13) are preferably made of ceramic, glass or a similar material.

Referring to FIG. 14, a probe 169 is illustrated, wherein elements common with those of the FIG. 12 embodiment are given the same reference number with a double prime (") added. The optical fiber length 139" is inserted into one end of a rigid cylindrical sleeve 171. The optical fiber 143", with which optical communication is desired to be made, is inserted in the opposite end of the cylinder 171. In order to hold the rigid cylinder 171 in place on the fiber 139", a piece of Teflon heat-shrinkable tubing 173 is shrunk around them. The sleeve 173 is chosen to have an inside diameter at the end that receives the fiber 143" to be slightly less than the fiber diameter. This provides a frictional engagement between the fiber and the probe 169 that holds the two pieces together. The entire structure is then covered by a jacket 175 having an inside diameter at its open end for guiding the fiber 143" during coupling. The jacket formed around the shrink tubing 173 and the fiber 139" also helps to keep all the components in place.

In order to improve the light coupling between the abutting optical fiber ends, in the probe embodiments of FIGS. 12-14, small lens elements may be provided on the ends of one or both of the abutting optical fibers. Such a modification is illustrated in FIG. 15. Two optical fibers 179 and 181 each have, respectively, a convex lens 183 and 185 attached to their ends. The result is to modify the conical angle of acceptance that is characteristic of an optical fiber end. As shown in FIG. 15, rays within the conical angle of acceptance are collimated by each of the lens elements for better coupling between the fibers.

Although the various aspects of the present invention have been described with respect to its preferred embodiments, it will be understood that the invention is entitled to protection within the full scope of the appended claims.

It is claimed:
1. A system for simultaneously measuring temperature and another physical parameter, comprising:
   a length of optical fiber transmission medium,
   means including a source of visible or near visible electromagnetic radiation pulses positioned at one end of said optical fiber medium for directing said radiation along said medium to another end thereof,
   a sensor positioned at said another end of said optical fiber medium in a manner to receive said source radiation, modulate it by the physical parameter and temperature being measured, and redirect the modulated radiation through the optical fiber medium to said one end thereof, said sensor comprising:
   a vibrating element in the path of said source radiation that is characterized by vibrating with either a frequency or an amplitude that is proportional to the magnitude of the physical parameter being measured, and
   a quantity of luminescent material also in the path of said source radiation, said luminescent material characterized by emitting, when excited, electromagnetic radiation having an intensity that decays, after termination of an excitation pulse from said excitation source, at a rate that is proportional to the temperature of the sensor, said source radiation being characterized by directing periodic pulses of radiation along said optical fiber medium, thereby exciting the luminescent material to emit a decaying electromagnetic radiation signal after each pulse as said modulated radiation, and means positioned at said one end of said optical fiber medium and receiving said modulated radiation for (1) measuring a function related to the time of the resulting luminescent radiation intensity decay after an excitation pulse, thereby to obtain an indication of the temperature of the sensor, and (2) measuring an intensity level of the decaying luminescent radiation intensity at an instant fixed with respect to an excitation pulse thereby to obtain an indication of the magnitude of the desired physical parameter.

2. The system of claim 1 wherein said optical fiber transmission medium comprises a single optical fiber.

3. The system of claim 1 wherein said detecting means additionally includes (3) means responsive to the indication of the temperature of the luminescent material for correcting the indication of the physical parameter to eliminate effects of sensor temperature variation upon said parameter indication.

4. A system for simultaneously measuring temperature and another physical parameter, comprising:
a length of optical fiber transmission medium,
means including a source of visible or near visible electromagnetic radiation pulses positioned at one end of said optical fiber medium for directing said radiation along said medium to another end thereof,
a sensor positioned at said another end of said optical fiber medium in a manner to receive said source radiation, modulate it by the physical parameter and temperature being measured, and redirect the modulated radiation through the optical fiber medium to said one end thereof, said sensor comprising:
  at least one optical element in the path of said source radiation whose optical properties vary in response to the magnitude of said physical parameter, and
  a quantity of luminescent material also in the path of said source radiation, said luminescent material characterized by emitting, when excited, electromagnetic radiation having an intensity that decays, after termination of an excitation pulse from said excitation source, at a rate that is proportional to the temperature of the sensor,
said source radation being characterized by directing periodic pulses of radiation along said optical fiber medium, thereby exciting the luminescent material to emit a decaying electromagnetic radiation signal after each pulse as said modulated radiation, and
means positioned at said one end of said optical fiber medium and receiving said modulated radiation for (1) measuring a function related to the time of the resulting luminescent radiation intensity decay after an excitation pulse, thereby to obtain an indication of the temperature of the sensor, and (2) measuring an intensity level of the decaying luminescent radiation intensity, at an instant fixed with respect to an excitation pulse thereby to obtain an indication of the magnitude of the desired physical parameter.

5. The system of claim 4 wherein said optical element of the sensor comprises means including a scintillation material for measuring ionizing radiation.

6. The system of claim 4 wherein said optical element of the sensor includes means altering the plane of polarization of radiation for measuring the magnitude of electric fields.

7. The system of claim 4 wherein said optical element of the sensor comprises means altering the plane of polarization of radiation for measuring the intensity of a magnetic field.

8. The system of claim 4 wherein said detecting means additionally includes (3) means responsive to the indication of the temperature of the luminescent material for correcting the indication of the physical parameter to eliminate effects of sensor temperature variation upon said parameter indication.

9. An optical sensor held at an end of an optical fiber and especially adapted for measurement of temperature of a surface, comprising:
an optically clear lens formed of a solid elastomeric material carried by said fiber end, and
a layer of luminescent material positioned on an outside surface of said lens in optical communication with said fiber end,
whereby said sensor may be positioned against the surface whose temperature is being measured to deform the elastomeric material and bring about a close contact between the layer of luminescent material and said surface.

10. The sensor according to claim 9 wherein said elastomeric material is characteristed by having significantly less heat conduction than that of said optical fiber.

11. The sensor according to claim 9 wherein said layer of luminescent material is held together by a binder of substantially the same material as said elastomeric lens.

12. The sensor according to claim 9 which additionally comprises means surrounding said sensor for blocking surrounding light from entering the optical fiber end.

13. A condition measuring system, comprising:
a length of an optical fiber communciation medium having first and second ends,
a sensor at said first end, said sensor including an optically clear lens formed of a solid elastomeric material carried by said one fiber end, and a layer of luminescent material carried on an opposite side of said elastometic lens from the side thereof being carried by said fiber first end,
means in optical communication with said second fiber communicating medium end for directing excitation radiation along said fiber to said luminescent material, and
means in optical communication with said second fiber communicating medium end for detecting a characteristic of luminescent radiation from said sensor that is related to said condition.

14. The system according to claim 13 wherein said elastomeric lens is characterized by changing the degree of optical coupling between the luminescent material layer and said fiber medium first end as the elastomeric lens is deformed, thereby to affect the amount of luminescence reaching said detecting means, and said detecting means including means for measuring both the temperature of the sensor luminescent material layer and pressure applied to said sensor by looking at different characteristics of luminescent radiation emitted by said luminescent material layer.

15. The system according to claim 14 wherein said luminescent material is characterized by emitting electromagnetic radiation in response to receiving excitation radiation, the emitted radiation decaying in intensity after termination of the excitation radiation, and wherein said excitation directing means includes means for directing periodic pulses of excitation radiation along said fiber, and further wherein said detecting means includes (1) means for measuring a characteristic of the resulting luminescent radiation decay as an indication of the temperature of said sensor, and (2) means for measuring absolute luminescent intensity at an instant fixed with respect to an excitation pulse as a measure of any force applied to said elastomeric lens.

16. A system for simultaneously measuring temperature and another physical parameter, comprising:
a length of optical fiber transmission medium,
means including a source of visible or near visible electromagnetic radiation positioned at one end of said optical fiber medium for directing pulses of said radiation along said medium to another end thereof,
a sensor positioned at said another end of said optical fiber medium in a manner to receive said source radiation, modulate it by the physical parameter and temperature being measured, and redirect the modulated radiation through the optical fiber medium to said one end thereof, said sensor comprising:
at least one mechanical element in the path of said source radiation whose position varies in response to the magnitude of the physical parameter being measured, and
a quantity of luminescent material also in the path of said source radiation, said luminescent material being characterized by emitting, when excited, electromagnetic radiation having an intensity that decays, after termination of an excitation pulse from said excitation source, at a rate that is proportional to the temperature of the sensor, and
means positioned at said one end of said optical fiber medium and receiving the decaying electromagnetic radiation from the sensor for (1) measuring a characteristic of the radiation intensity decay emitted by the luminescent material, thereby to obtain an indication of the temperature of the luminescent material, and (2) measuring an intensity level of the decaying radiation emitted by the luminescent material at an instant that is fixed with respect to the occurance of an excitation pulse, thereby to obtain an indication of the magnitude of the desired physical parameter.

17. The system of claim 16 wherein said optical fiber transmission medium comprises a single optical fiber.

18. The system of claim 16 wherein the mechanical element of said sensor is characterized by being statically displaced an amount proportional to the magnitude of the physical parameter being measured.

19. The system of claim 16 wherein said luminescent material is attached to the mechanical element in a region that is illuminated by said source radiation.

20. The system of claim 16 wherein said detecting means additionally includes (3) means responsive to the indication of the temperature of the luminescent material for correcting the indication of the physical parameter to eliminate effects of sensor temperature variation upon said parameter indication.

21. A method of measuring the temperature of a surface, comprising the steps of:
providing a sensor having a solid elastomeric convex lens carried by an end of an optical fiber communication medium and a thin layer of luminescent material attached to an outer surface of the lens in a position that is in optical communication with said optical fiber end, said luminescent material being characterized by emitting, when excited, electromagnetic radiation having a detectable characteristic that varies as a function of its temperature,
urging said luminescent material layer against said surface by applying force thereagainst through the optical fiber sufficient to deform the elastomeric lens by compression, thereby providing intimate contact between the luminescent material and said surface,
directing exciting radiation through said fiber and lens onto said luminescent material, thereby causing emissions of electromagnetic radiation having a characteristic that varies as a function of temperature to be emitted by said luminescent material and passed back through the optical fiber communication medium, and
detecting the emitted luminescent radiation that passes back through said lens and said optical fiber communication medium, whereby a signal is obtained that is related to the temperature of the surface.

22. A method of measuring the pressure within a fluid medium, comprising the steps of:
positioning a sensor within said fluid medium, said sensor having (1) a solid elastomeric convex lens carried by an end of an optical fiber communication medium, (2) a layer of luminescent material attached to an outer surface of the lens in optical communication with said optical fiber end, said luminescent material being characterized by emitting luminescent electromagnetic radiation when excited, and (3) means surrounding said elastomeric element for sealing a space around said lens and luminescent material, said sealing means including a flexible diaphragm positioned across said lens in a manner that differences in pressure between said sealed space and said fluid medium surrounding the sensor causes the elastomeric element to be deformed,
directing exciting radiation through said fiber and lens onto said luminescent material, thereby causing electromagnetic radiation to be emitted by said luminescent material and passed back though the optical fiber communication medium in an amount dependent upon the degree of deformation of the lens and thus upon the pressure difference between that of the sealed sensor space and that of the fluid medium surrounding the sensor, and
detecting a level of emitted luminescent radiation that passes back through said lens and said optical fiber communication medium, whereby a signal is obtained that is related to the pressure of the fluid medium.

23. An optical sensor held at an end of an optical fiber and especially adapted for measurement of temperature and force, comprising:
- an optically clear lens formed of a solid elastomeric material carried by said fiber end, and
- a layer of luminescent material positioned on an outside surface of said lens in optical communication with said fiber end,
- whereby said sensor may be positioned in an environment wherein any force applied to said lens causes its deformation and a resulting detectable change in optical coupling between the luminescent material and said fiber end and wherein the luminescent material emits optical radiation proportional to its temperature.

24. The sensor according to claim 23 which additionally comprises means surrounding said elastomeric lens for sealing a space around said lens, said sealing means including a flexible diaphragm positioned across said lens so that differences in pressure between said sealed space and a space surrounding the sensor cause the elastomeric lens to be deformed.

* * * * *

UNITED STATES PATENT AND TRADEMARK OFFICE
CERTIFICATE OF CORRECTION

PATENT NO. : 4,752,141

DATED : June 21, 1988

INVENTOR(S) : Sun et al.

It is certified that error appears in the above-identified patent and that said Letters Patent is hereby corrected as shown below:

```
Col. 17, line 18:  insert --,-- after "pulse";
         line 55:  "radation" should be --radiation--;
         line 68:  delete the ",";
Col. 18, line  1:  insert --,-- after "pulse";
         line 35:  "characteristed" should be --characterized--;
         line 47:  "communciation" should be --communication--;
         line 53:  "elastometic" should be --elastomeric--.
```

Signed and Sealed this

Twenty-fifth Day of October, 1988

Attest:

DONALD J. QUIGG

*Attesting Officer*     Commissioner of Patents and Trademarks